United States Patent [19]

Pader

[11] 4,152,418

[45] May 1, 1979

[54] ZINC AND ENZYME MOUTHWASH AND MOUTHWASH CONCENTRATE FOR REDUCING DENTAL PLAQUE AND CALCULUS FORMATION

[75] Inventor: Morton Pader, West Englewood, N.J.

[73] Assignee: Lever Brothers Company, New York, N.Y.

[21] Appl. No.: 856,469

[22] Filed: Dec. 1, 1977

Related U.S. Application Data

[60] Division of Ser. No. 737,260, Oct. 29, 1976, Pat. No. 4,082,841, which is a continuation of Ser. No. 621,331, Oct. 10, 1975, abandoned, which is a continuation of Ser. No. 479,914, Jun. 17, 1974, abandoned, which is a continuation of Ser. No. 308,079, Nov. 20, 1972, abandoned, which is a continuation-in-part of Ser. No. 214,497, Dec. 30, 1971, abandoned, which is a continuation of Ser. No. 24,882, Apr. 1, 1970, abandoned.

[51] Int. Cl.² ............................................. A61K 7/28
[52] U.S. Cl. .................................................... 424/50
[58] Field of Search ........................... 424/48, 58, 94

[56] References Cited

U.S. PATENT DOCUMENTS

| | | | |
|---|---|---|---|
| 1,018,240 | 2/1912 | Foregger | 424/53 |
| 1,435,498 | 11/1922 | Resnik | 424/53 |
| 1,488,097 | 3/1924 | Creger | 424/55 |
| 1,627,963 | 5/1927 | Fuller | 424/55 X |
| 1,767,667 | 6/1930 | Gray | 424/145 |
| 2,004,957 | 6/1935 | Messner | 424/38 |
| 2,236,828 | 4/1941 | Muncie | 424/56 |
| 2,527,686 | 10/1950 | Sandberg | 424/50 |
| 3,696,191 | 10/1972 | Weeks | 424/50 |
| 4,022,880 | 5/1977 | Vinson et al. | 424/49 |
| 4,082,841 | 4/1978 | Pader | 424/50 |

FOREIGN PATENT DOCUMENTS

| | | | |
|---|---|---|---|
| 87896 | 4/1922 | Austria | 424/50 |
| 959764 | 12/1974 | Canada. | |
| 961412 | 1/1975 | Canada. | |
| 1467790 | 12/1968 | Fed. Rep. of Germany | 424/56 |
| 2203379 | 8/1972 | Fed. Rep. of Germany | 424/50 |
| 4675M | 12/1966 | France | 424/50 |
| 7102423 | 8/1972 | Netherlands | 424/50 |
| 7100701 | 8/1972 | South Africa. | |
| 689679 | 4/1953 | United Kingdom | 424/56 |
| 1033229 | 6/1966 | United Kingdom | 424/50 |
| 1197164 | 7/1970 | United Kingdom | 424/50 |
| 1290627 | 9/1972 | United Kingdom | 424/50 |
| 1296952 | 11/1972 | United Kingdom | 424/50 |
| 1373001 | 11/1974 | United Kingdom | 424/50 |
| 1373003 | 11/1974 | United Kingdom | 424/50 |

OTHER PUBLICATIONS

Chem. Abstracts 83, #48204k(1975) of Canada 959764 Pader, Morton.
Chem. Abstracts 78, #115218e(1973) of So. Africa 7100701 Pader, Morton.
Chem. Abstracts 83, #33041f(1975) of Canada, 961412, Vinson & Canero.

*Primary Examiner*—Shep K. Rose
*Attorney, Agent, or Firm*—Kenneth F. Dusyn

[57] ABSTRACT

There is disclosed in this specification an improved composition for reducing dental plaque and calculus formation, comprising zinc ions and an organoleptically acceptable enzyme, which may be a protease, carbohydrase, or lipase, or mixtures of these enzymes.

11 Claims, No Drawings

ZINC AND ENZYME MOUTHWASH AND MOUTHWASH CONCENTRATE FOR REDUCING DENTAL PLAQUE AND CALCULUS FORMATION

This application is a divisional of Ser. No. 737,260, filed Oct. 29, 1976, U.S. Pat. No. 4,082,841, Apr. 4, 1978; which is a continuation of Ser. No. 621,331, filed Oct. 10, 1975, abandoned; which is a continuation of Ser. No. 479,914, filed June 17, 1974, abandoned; which is a continuation of Ser. No. 308,079, filed Nov. 20, 1972, abandoned; which is a c-i-p of Ser. No. 214,497, filed Dec. 30, 1971, abandoned; which is a continuation of Ser. No. 24,882, filed Apr. 1, 1970, abandoned.

BACKGROUND OF THE INVENTION

1. Field of the Invention

The present invention concerns combinations of zinc compounds furnishing zinc ions and one or more enzymes which may be a protease, a carbohydrase, or a lipase, or mixtures thereof.

Dental plaque forms as a deposit on and around teeth. It is a product of microbial growth, a dense microbial layer consisting of a mass of microorganisms embedded in a matrix, which accumulates on the tooth and adjacent surfaces. It has been reported that the microorganisms immediately after dental prophylaxis are mainly coccoidal organisms, which, in the mouths of some persons at least, change to filamentous organisms after a few days.

A wide variety of microorganisms are found in the oral cavity, some of which can produce acids or toxic materials. In addition to these microorganisms, dental plaque is composed of many other substances, such as mucoproteins and minerals derived from saliva, dead cells, and food residues which are dissolved, or present in particulate form. A major binding force holding plaque together is a matrix formed of the aforementioned mucoprotein or sticky polysaccharide substances secreted by some types of microorganisms.

Plaque deposition varies in extent throughout the oral cavity. Larger amounts tend to accumulate on those less accessible and more sheltered areas of teeth which cannot readily be reached with a toothbrush; rinsing with water alone usually will not dislodge such plaque. Plaque may also develop in pits and fissures of the teeth. It is extremely difficult to remove such plaque by mechanical means. With growth and multiplication of the bacteria, the plaque increases in size and becomes more viscous and thicker. The situation is exacerbated by the production by some microorganisms of a polysaccharide slime.

Recent dental research points to the fact that the major potential for harm by plaque resides in the bacterial component thereof. Bacterial metabolism can result in the production of acids, toxins and enzymes which are deleterious to the neighboring oral tissues. These materials can be retained in the mucoprotein matrix of the plaque and thus exert a direct influence on the adjacent tooth structures and gingivae. There is evidence pointing to plaque as being a direct cause of caries due to the generation of acids within its structure. Also, a direct correlation has been observed between the presence of dental plaque and the occurrence of gingivitis.

Dental calculus is a calcified or calcifying mass which is generated from dental plaque. In its more advanced state, it consists of an organic matrix, representing about 20% of the deposit and containing carbohydrates, proteins, bacteria, cellular debris, and other organic materials. The major portion of calculus is inorganic. This portion contains calcium, phosphorus, magnesium and lesser amounts of other mineral elements. The calcium and phosphorus are present primarily in the form of various calcium phosphate species, the most common of which is hydroxyapatite.

There are at least two well-recognized stages in calculus formation. First, the organic matrix or mucilaginous plaque (individually or simultaneously) deposits upon the tooth enamel or cementum, and may spread to adjacent areas in the oral cavity. At this stage, vigorous oral hygiene, especially tooth brushing, can remove much of the deposit and effectively reduce the amount of calculus subsequently found. In the second stage, alterations occur within the plaque which initiate mineralization. The exact mechanism whereby mineralization occurs has not yet been determined. Plaque tends to accumulate, selectively, calcium and phosphate. In one theory, it has been suggested that it is the activity of the microorganisms within the plaque which leads directly to the formation of dental calculus. Of the various types of bacteria present, the Leptothrix and Actinomyces appear to have been implicated most directly as being involved in both intercellular and extracellular mineralization. In another theory, it has been proposed that under appropriate conditions the mucilaginous matrix of the dental plaque is so altered as to promote mineralization. Here, too, the role of bacteria appears to be important; it has been observed that mineralization can start near the bacteria and that the bacteria are able to manufacture materials which are able to initiate the formation of insoluble calcium salts.

The clinical importance of plaque and calculus has been demonstrated many times over and an association between calculus and the occurrence of periodontal disease has long been observed. Removal of calculus is one of the most commonly practiced preventive measures against periodontal disease. As mentioned above, recent findings point toward plaque being involved in both carious lesion formation and in the initiation of periodontal disease even in the absence of calculus development. Thus, a direct correlation has been made between the appearance of plaque and gingivitis even in the absence of calculus.

2. The Prior Art

Prior to the instant invention, attempts have been made by others to retard the accumulation of dental calculus by means of zinc salts. M. T. Hanke in the Journal of the American Dental Association, Volume 27, September, 1940, page 1388, describes experiments to combat plaque with mouthwashes containing a variety of metallic salts, including zinc salts, having antifungal properties. The work of Hanke leads to the conclusion that the use of a zinc salt such as Hanke employed as the sole therapeutic agent has serious drawbacks, and that such zinc salts alone generally are not effective.

Also known is the use of soluble zinc salts as germicidal and deodorizing compounds, as set forth in U.S. Pat. No. 1,593,485 to Crosnier. This patent discloses that mixtures of zinc sulfophenate (i.e., phenolsulfonate) and zinc sulfate, chloride, or acetate are useful as bactericides and deodorants, the latter property being of value in slaughter-houses and the like where hydrogen sulfide is generated. However, there is no suggestion in this patent, nor in any other art known to the inventor, that a combination of zinc ions and an enzyme has unusually effective antiplaque and/or anti-calculus properties.

The enzyme preparations tested in the past as plaque/calculus inhibitors have been of microbial, animal or vegetable origin. Crude mixtures of enzymes from various origins have also been used. Such mixtures have contained proteolytic, amylolytic and lipolytic activities. In some instances, the enzyme preparations tested have been relatively pure. The rationale for their use has been the hope that they could disrupt the plaque matrix or other structural component of plaque.

Enzyme preparations have found practical application in one instance, namely, the incorporation of such a material in a chewing gum vehicle, as disclosed in U.S. Pat. No. 3,235,460 to Ennever, wherein the use of pancreatin is discussed. The normal use of the chewing gum vehicle insures prolonged contact of the enzyme with the substrates it is intended to attack. Prolonged contact is required to obtain the proteolytic action of the product of Ennever's invention, which provides only 30% reduction in calculus after 8 weeks during which there was 25 minutes' contact per day.

The major difficulty in the practical use of enzymes as plaque and calculus inhibitors in other dental preparations is the need to realize rapid action at relatively low enzyme concentration, since dental preparations such as mouthwashes, toothpastes, tooth powders, etc. do not in their normal use involve the prolonged contact inherent in the use of enzymes contained in a chewing gum vehicle.

U.S. Pat. No. 3,194,738 to Harrisson and Packman discloses the use of enzymes in such vehicles as chewing gums, toothpastes, tablets, and mouthwashes, for retarding calculus formation.

U.S. Pat. No. 2,527,686 discloses a mouthwash containing about 0.16% zinc chloride, and about 16% total of a mixture of Papain and Malt.

SUMMARY OF THE INVENTION

It has now been discovered that dental plaque and calculus can be greatly reduced by contacting the teeth for a relatively short time with a combination of zinc ions and an enzyme, which may be a protease, a carbohydrase, or a lipase, or mixtures thereof. The combination of zinc salt with various enzymes has been found experimentally to be so active as an antiplaque and anticalculus agent to demonstrate practical efficacy for the control of plaque and calculus formation, i.e., to be effective under oral hygiene regimens under which prior art preparations showed only a low order of efficacy.

In its broad aspect, the invention comprises a composition suitable for reducing dental plaque or calculus, comprising a zinc compound capable of furnishing zinc ions, and an enzyme.

In another aspect, the invention comprises an orally acceptable medium having incorporated therein a zinc compound capable of furnishing zinc ions in the oral cavity, and an enzyme which may be a protease, a carbohydrase, or a lipase, or mixtures thereof.

Still another aspect embodies a dentifrice in paste form containing, as a plaque and calculus inhibitor, a combination of zinc ions and an enzyme.

A further embodiment of the invention provides a process for reducing dental plaque and calculus on a dental substrate, which may be a human tooth in vivo, or a denture, comprising contacting the dental substrate with a composition of the instant invention.

The mechanism whereby zinc salts and appropriate enzymes can retard the development of plaque and calculus has not yet been elucidated. Thus, the following represents theory, to which I do not desire to be bound.

It is hypothesized that the major action of zinc ion in the present invention is interference with two stages in the development of calculus, namely (1) structure formation of the plaque and (2) mineralization of the plaque. Both of these processes will make the plaque more cohesive and thereby, less permeable to penetration from the oral environment of large molecules. Zinc interferes with the attachment of the microbial elements to each other and to the mucilaginous matrix, as well as with the deposition of the matrix and also can interfere with the calcification stage. In both stages the zinc probably acts as an antagonist to calcium ions; calcium ions have been implicated frequently in protein-to-protein bonding and related phenomena. It is postulated that a zinc salt, by preventing the plaque from becoming dense and strongly cohesive, permits more ready attack on the cohesive structures within the plaque by enzymes which are applied thereto, and perhaps even make the plaque permeable enough to allow penetration by the relatively large enzyme molecules. The enzymes, being in close contact with their substrate, can then effectively and efficiently destroy it. Destruction of the substrate will result in a non-cohesive mass which can be readily washed away by simple rinsing, salivary flow, toothbrushing, etc. The plaque structural components have not yet been clarified in detail. The proven presence of proteinaceous and carbohydrate elements, however, may be the reason for attack on plaque by proteolytic enzymes and enzymes able to degrade various types of carbohydrates and mucopolysaccharides. The high efficacy of lipolytic enzymes in hibiting calculus formation still requires explanation.

It will be understood that our discovery concerns the co-action of zinc ions and an enzyme, rather than a well-defined synergistic property. With respect to all the combinations falling within the invention, the high antiplaque/anticalculus activity could not be routinely achieved by using high levels of either class of active material, because of the nature of their action, as described hereinbefore. Nor could very high levels of either class be used in an oral composition, since high levels of zinc ions would be too astringent, and high levels of certain enzymes might attack mucosal tissue. By using mixtures of the two classes however, advantage is taken not only of their co-action, but also of the fact that low levels of each class can be employed, i.e., levels sufficiently low to be orally acceptable while at the same time providing, by their combination, highly effective antiplaque and anticalculus activity, a requirement for conventional self-use.

In accordance with the present invention, oral preparations are contemplated containing in the order of from 0.1% to 30% zinc salts. In addition, there will be present an amount of hydrolytic enzyme which in coaction with zinc ions is effective to retard plaque and calculus formation. The amount of such an enzyme which is effective to inhibit plaque and calculus formation, will obviously, depend upon the activity of the enzyme, as well as its concentration.

The balance of the oral preparation in accordance with the present invention will consist of the usual carrier media, and other substances which may be desired. For example, where the oral preparation contemplated is a mouthwash, the balance of the preparation will consist essentially of water, or water and a mono- or polyhydric alcohol such as ethanol, glycerol, or sorbitol, and optionally and usually, flavoring substances and foaming agents. The glycerine and sorbitol are also useful as an aid in sweetening the product. Surfactants or suspending agents are usually present in mouthwashes as solubilizers for essential flavoring oils. The customary solubilizers for this purpose are the sorbitan fatty acid esters, the polyoxyethylene derivatives thereof and polyoxyethylene fatty acid ethers. In addition, the mouthwash formulation may contain one or more of the well-known, highly active antibacterial agents, such as neomycin sulfate, hexachlorophene, the halogenated salicylanilides, compatible quaternary ammonium compounds, and the like.

In the formulation of the mouthwash, it is within the scope of this invention to provide compositions which contain suspended active agents, whether they be enzyme or zinc compound.

When the oral composition is a toothpaste, there may be present polishing agents, flavoring substances, sweetening substances, foaming agents, etc. It will be understood that the polishing agents and other components suitable for use in the toothpastes of the invention must be compatible with both the zinc compounds and enzymes.

Among the suitable inorganic polishing agents useful in accordance with the invention are silica xerogels and silica aerogels manufactured by the Davison Chemical Division of W. R. Grace and Co. under the trade names of Syloid 63, Syloid 65 (xerogels) and Syloid 244 (aerogels). The xerogels are synthetic, aggregated, amorphous, highly porous silicas having generally a mean particle diameter of about 4 to 10 microns. The aerogel Syloid 244 has a mean particle diameter of about 3 microns and is more porous than are the xerogels. Also useful are other polishing agents disclosed hereinafter.

The polishing agent should be in the form of fine particles, as is well known in the art. Preferably, the particles should be of such size that at least 40% pass through a 325 mesh screen, and at least 90% pass through a 20 mesh screen. The finer particles within this size range are preferred, particularly a size distribution such that all the particles pass through a 20 mesh screen, more than 90% pass through a 100 mesh screen, more than 80% pass through a 200 mesh screen, and more than 40% pass through a 325 mesh screen. Especially preferred are the finer particles having a mean particle diameter of about 3 to about 44 microns.

Polymer particles of various types are useful as abrasives. A particularly useful polymer is polyethylene in powder form of such size that more than 40% passes through a 325 mesh screen, more than 80% passes through a 200 mesh screen, at least 85% passes through a 100 mesh screen, and 90 to 100% passes through a 20 mesh screen. Such polyethylene polymers are sold under the names of Super Dylan polyethylene J-1 or J-2 powder.

Other substances proposed as dental abrasives include various abrasive materials such as silica imbedded in protective plastic particles.

Polishing agents will be present in the toothpastes of our invention over the broad range of about 1% to 70%, preferably 10% to 60%, and typically from about 20% to 50%. In a tooth powder the polishing agent will be present over the range of about 50% to 99%, preferably about 70% to 95%, and typically from about 90% to about 95%.

The toothpastes will usually contain compatible bodying agents such as gum Karaya, gum Tragacanth, starch, sodium carboxymethylcellulose, Irish moss, gum arabic, sodium carboxymethylhydroxyethylcellulose, polyvinylpyrrolidone, etc. When present, these will usually be at levels of from about 0.5% to about 3%, preferably from about 0.8% to about 1.5%. Obviously, they must resist degradation by the enzyme component of the composition.

Humectants are desirable in a toothpaste. These will usually be such compounds as glucose, honey, glycerol, propylene glycol, sorbitol, polyethylene glycol 400, and other polyhydric alcohols, and may be present in the composition in amounts up to about 80% by weight.

High levels of humectant in a toothpaste, with little or no water, will tend to favor greater stability of the enzyme, in view of the well-known tendency of enzymes to deteriorate in an aqueous medium unless appropriate precautions are taken.

Other adjuvants may be present, such as fluorine compounds, chlorophyll compounds, flavor substances, saccharin, urea, ammonium compounds, alcohol, mineral oil, foaming agents or detergents, such as sodium lauryl sulfate, dodecanesulfonate, acyl taurines, acyl isethionates, etc., depending upon the form of the product. The protein nature of enzymes makes them susceptible to denaturation and inactivation by surface active agents, and accordingly these materials should be used with care.

By "zinc ion" is meant the zinc-atom portion of the molecule of a zinc compound in the solid or undissociated state, and capable of being dissociated into simple or complex zinc ions at temperatures of about 37° C., as well as to simple or complex zinc ions formed in an aqueous medium such as a mouthwash or oral salivary secretions.

Zinc ions may be furnished by any pharmaceutically acceptable zinc salt having sufficient solubility in an aqueous medium to provide an effective level of zinc ions, i.e., zinc cations, at the site of action of the zinc ion. The remainder of the molecule of the zinc salt may be inert for antiplaque and anticalculus purposes.

The term "pharmaceutically acceptable" as used herein with reference to zinc compounds, is applicable to those compounds which, under the conditions of use and in the compositions set forth herein, are safe and organoleptically tolerable in the oral cavity, and have no significant side effects either orally or systemically.

In mouthwashes it is preferred to use the more soluble zinc salts, e.g., those having a solubility in water at 20° C. of the equivalent of at least about one gram of Zn per 100 ml. of water. A particularly preferred zinc compound is zinc phenolsulfonate, because it is virtually insensitive to pH change, for example to the adjustment of the pH of a mouthwash to near neutrality, with respect to hydrolysis and precipitation. In toothpastes, the less soluble zinc salts are preferred, since more can be incorporated without excessive astringency.

Zinc compounds having the low solubility of zinc oxide (about $1.6 \times 10^{-4}$ ZnO equivalent to about 1.3 gm $Zn^{++}$ per 100 ml water at 29° C.) or zinc stearate (about $1 \times 10^{-7}$ gm zinc stearate, equivalent to about $1 \times 10^{-8}$ gm $Zn^{++}$ per 100 ml water) exhibit excellent effectiveness in conjunction with an enzyme in accordance with the invention. Zinc compounds having a solubility in water as low as the equivalent of about $1 \times 10^{-8}$% zinc may be used, as well as those having solubilities ranging from the aforesaid level up to that of the most soluble zinc compounds, for example that of zinc bromide, which is about 447 grams (equivalent to about 130 grams Zn++) per 100 ml at 29° C. The terms "zinc compound" or "zinc salt" as used herein are intended to exclude enzyme-bound zinc, and refer only to non-enzyme-bound, pharmaceutically acceptable zinc compounds and zinc salts added in addition to the enzyme components.

The solubilities and zinc contents of zinc compounds having utility in accordance with the instant invention may be derived from data readily obtainable in the literature.

Examples of the compounds that may be employed are zinc salts of the following organic and inorganic anions: acetate, benzoate, borate, bromide, carbonate, citrate, chloride, fluoride, hexafluorosilicate, dl-lactate trihydrate, phenolsulfonate, silicate, alkanoates having 8 to 18 carbon atoms, salicylate, stannate, sulfate, tannate, titanate, zinc salicylate, zinc oxide, zinc hydroxide.

The enzymes useful in the practice of this invention are those well known catalytically active protein substances within the class of hydrolases, which break down or hydrolyze proteins (proteases), carbohydrates (carbohydrases), fatty substances (lipases), or complexes of these types of substances. These enzymes and the crude enzyme preparations containing them are obtained from natural sources or by the action of microorganisms on an appropriate medium having a nitrogen source and a carbon source. For example the microorganism *Bacillus subtilis* when cultivated in a medium containing a protein, such as soybean meal, and glucose, produces a proteolytic enzyme suitable for use in accordance with the invention. One useful protease thus prepared has an activity of about 2.4 million units per gram at pH 7 when assayed against a casein substrate as described hereinafter.

A carbohydrase may be produced during the culture of *Aspergillus oryzae* on a medium containing soybean meal, and a soluble starch.

A lipase may be formed by *Mucor lipolyticus* when cultured in a suitable medium of corn steep liquor and olive oil.

Suitable enzymes may be produced by other microorganisms and in other media well known to those skilled in the art.

Examples of enzymes obtained from natural sources are pancreatin from hog pancreas, trypsin from hog and beef pancreas, papain from papaya latex, and Lipase 448 from hog pancreas.

The term "enzyme preparation" as used herein refers to enzymatic substances that may contain as high as 100% pure enzyme or may contain a very low level of enzyme, for example 1%, or even less. The word "enzyme" as used herein applies to the active enzymatic principle of the "enzyme preparation".

Useful treatises on enzymes are Kirk-Othmer, Encyclopedia of Chemical Technology, Second Edition, Volume 8, pages 173–230, and Thomas E. Barman's "Enzyme Handbook", Volume II, (1969), Springer-Verlag, New York, Inc.

Commercial enzyme preparations generally are not as pure, i.e., do not have as high a specific activity, as is theoretically possible. Commercial preparations usually contain from about 2% to about 80% by weight of enzyme, the balance being non-enzyme-active substances including water, inert solid matter such as sodium or calcium sulfate or chloride, or other solid matter added during manufacture, and generally also contain inert matter associated with the source material.

It is important, therefore, in formulating products of the invention to take into account both the activity of the enzyme preparation as well as its total amount. Generally, formulations will be based on activity, not on total weight of enzyme preparation. For organoleptic reasons, it is preferably to formulate with relatively pure enzyme preparations. However such preparations usually are more costly than cruder ones, and the latter may also be employed. When partially purified enzyme preparations are incorporated, one must ascertain that the non-enzyme materials associated with the enzyme preparation do not contribute off-flavors, do not have adverse effects on texture or appearance, or do not interfere significantly with the enzyme activity.

The enzymes to be employed in the mouthwash compositions of the invention must be cosmetically acceptable. This term describes enzymes that are substantially free from extraneous substances that are associated with the naturally crude enzyme preparation which may impart undesirable flavor, color, or other characteristics to the mouthwash. Usually the suitable enzymes are those that have been purified and separated from such associated substances as animal, vegetable, or grain tissue, flavor or color bodies, water insoluble substances, etc. The enzyme preparations for use in mouthwashes will preferably form substantially clear aqueous compositions.

The enzyme preparation may be used as an aqueous slurry or may be used in particulate form.

The level of enzyme in the enzyme preparations useful in the practice of this invention is not critical, and the amount of enzyme preparation will be at least sufficient to coact with zinc ions to provide an improved antiplaque and anticalculus mixture, as set forth in detail hereinafter.

It is well known that the activities of some enzymes, for example gluconolactonase, phosphoglycollate phosphatase, phospholipase C, carnosinase, ureidosuccinase, variously are enhanced by the presence of metal cations such as zinc, calcium, barium, magnesium, manganese, cobalt, lithium, cerium, and chromium, and that these cations either are found naturally associated with, or known to be a requirement for activity of some enzymes.

The amount of zinc ion in known zinc-dependent enzymes however is too small to produce a coating effect on plaque and calculus.

On the other hand it is known that zinc has an inhibiting effect on some enzymes.

One method for determining the protease activity of the toothpastes of this invention is by assay against denatured hemoglobin (supplied by Nutritional Biochemicals Corporation). In suitable proportions, the toothpaste is allowed to react with an aqueous hemoglobin solution for 20 minutes at 55° C. whereupon the reaction is stopped by the addition of trichloroacetic acid. The solution is filtered through a Whatman No. 42 filter paper and the absorbance of the filtrate is measured against a hemoglobin blank in 1 cm. cells in a spectrophotometer at a wavelength of maximum absorbance near 280 m$\mu$. The enzyme activity is assessed in terms of the degree to which the hemoglobin has been degraded. One unit of protease activity is defined as one unit change in optical density during 20 minute incubation at 55° C.

Dextranase activity can be determined by allowing the enzyme preparation to act on clinical grade dextran having a molecular weight of 200,000 to 300,000 obtainable from General Biochemicals, dissolved as a 2.5% solution in 0.1 M sodium acetate at pH 5.4. After reacting at 40° C. for 20 minutes, a 1% alkaline solution of 3,5-dinitrosalicylic acid monohydrate is added, the solutions placed in boiling water for 5 minutes, cooled, and the optical density determined at 540 m$\mu$. The activity is expressed in maltose units, one unit being the number of milligrams of maltose per hour formed at pH 5.4 at a temperature of 40° C.

The amylase activity of the compositions of this invention can be determined for example by allowing 1 ml. of a 1% aqueous dispersion of the toothpaste to act upon 2 ml. of a 1.5% suspension of insoluble potato starch in a pH 7.0 phosphate buffer. After 10 minutes, 2.5 ml. of an alkaline solution containing 1% 3,5-dinitrosalicylic acid color reagent is added, the mixture boiled for 5 minutes, cooled, diluted with 10 ml. water, centifruged for 10 minutes at 3500 rpm, and the optical density of the supernatant liquid read on a spectrophotometer at 540 m$\mu$. One unit of amylase activity is defined as one unit change in optical density during 20 minutes incubation at room temperature.

Lipase activity may be assayed as described in "Archives of Biochemistry and Biophysics," Volume 83, pages 309-319 (1959). The lipase is allowed to act on neutralized olive oil, and the resulting acidity neutralized by maintaining the pH constant at 9.0 with 0.1 N NaOH over a period of time. The lipase unit is defined as the amount of enzyme which liberates under the conditions of the test 10 milliequivalents of acid per minute.

Enzyme AP, used in Examples 2 and 4, is an enzyme preparation whose activity is mainly proteolytic. Enzyme AP is a trademark of the Monsanto Chemical Co. It has an activity of 2.4 million neutral protease units per gram, determined by testing against a casein substrate. In the test procedure, the casein is digested under controlled conditions, and after a pre-determined time limit, the reaction is stopped by the addition of trichloroacetic acid. The solution is filtered, Folin reagent added, and the amount of color developed is measured spectrophotometrically and the level of enzyme activity determined therefrom. The activity is expressed in neutral protease units calculated by comparison with a standard tyrosine solution.

Among the proteases useful in accordance with this invention are:

| | |
|---|---|
| Alcalase | — (trademark) a hydrolytic enzyme preparation whose major activity is proteolytic. It is derived from *Bacillus subtilis* and is obtainable from Novo Industri A/S. Purification of the commercial detergent-grade material is desirable before use in an oral preparation |
| Maxatase | — (trademark) obtainable from Chas. Pfizer, Inc. |
| Protease AP-100 | — (trademark) obtainable from Monsanto Chemical Company |
| Prolase 300 | — a trademark of the Wallerstein Company. |
| trypsin | — may be derived from bovine or porcine pancreas. |
| chymotrypsin | — may be derived from bovine, chicken, or turkey pancreas. |
| papain | — may be obtained from the milky latex of the Papaya tree. |
| ficin | — may be obtained by extraction from the fruit of a tropical fig tree. |
| bromelin | — produced by the family Bromeliaceae obtainable from pineapple and pineapple plant. |
| M-Zyme | — derived from a microbiological source. Has keratinase activity. |
| Rhozyme P-11 | — (trademark) derived from fungal sources. Obtainable from Rohm and Haas. |

Among the useful carbohydrases are:

| | Among the useful carbohydrases are: |
|---|---|
| dextranase | — may be derived from Aspergillus sp. |
| cellulase | — may be derived from *Myrothecium verrucaria* |
| Cellzyme A alpha-amylase, beta-amylase, and mixtures thereof | — a crude cellulolytic enzyme system. |
| | — may be obtained from *Bacillus subtilis*. |
| Mylase 100 | — (trademark) derived from *Aspergillus oryzae*. Obtainable from the Wallerstein Company. |
| Mylase W | — (trademark) a mixture of amylase, dextranase and other enzymes derived from a fungal source. Obtainable from the Wallerstein Company. |
| Amylase L-661 | — (trademark) obtainable from Premier Malt Products, Inc. |
| Fungal Amylase | — (trademark) obtainable from the Marschall Division of Miles Laboratories, Inc. |

| | Among the lipases useful in the invention are: |
|---|---|
| Lipase 4000 | — (trademark) may be derived from *Aspergillus oryzae*. |
| Lipase B | — (trademark) |
| Lipase 448 | — (trademark) a relatively pure lipolytic enzyme derived from hog pancreas. One gm. digests 448 gm. of fat (av. mw = 840) per hour at pH 7.8 and a temperature of 37° C. Obtainable from Nutritional Biochemicals Corp. |
| gastric lipase | |
| pancreatic lipase | |
| plant lipases | |

Typical oral preparations embodying the present invention are the following:

| Mouthwashes | Broad Range | Preferred Range |
|---|---|---|
| zinc compound | 0.01% to 5% | 0.2%-3% |
| enzyme preparation | 0.0001% to 5% | 0.002%-3% |
| surfactants and suspending agents | 0% to 2% | 0.5%-1% |
| glycerine, sorbitol, etc. | 0% to 50% | 5%-20% |
| water | q.s. to 100% | q.s.-100% |
| plus flavors, colorants, germicides and the like, as desired | | |
| Tooth Powders | | |
| zinc compound | 0.1% to 30% | 0.2%-20% |
| enzyme preparation | 0.1% to 30% | 0.2%-20% |
| foaming agent | 0% to 10% | 0.5%-2% |
| dental polishing agent | 50% to 99% | 70%-95% |
| plus flavors, colorants, germicides and the like, as desired | | |
| Toothpastes | | |
| zinc compound | 0.1% to 20% | 1%-10% |
| enzyme preparation | 0.1% to 20% | 1%-5% |
| foaming agent | 0% to 5% | 0.5%-3% |
| dental polishing agent | 1% to 70% | 10%-60% |
| humectants and water | 30% to 80% | 35%-55% |
| plus flavors, colorants, germicides and the like, | | |

-continued as desired

Generally, the activity of enzymes is maintained better if the storage is at low temperature. It is thus within the scope of this invention to provide mouthwash compositions comprising zinc salts and enzymes in an aqueous medium which must be stored under refrigerated or frozen conditions. There may also be provided liquid mouthwash compositions comprising zinc salts and enzymes suspended in non-aqueous orally acceptable media (e.g. glycerine, ethyl alcohol, propylene glycol, 1,3-butylene glycol, etc.) which are diluted with water immediately prior to use, or there may be provided mouthwashes in dry solid form, which are reconstituted with water immediately prior to use.

When the product of the invention is a toothpaste, it comprises about 0.1% to about 20% of a zinc compound capable of furnishing zinc ions, and about 0.1% to about 20% of an enzyme preparation selected from the group consisting of proteases, carbohydrases, lipases, and mixtures thereof, said zinc compound and said enzyme preparation being incorporated in a compatible toothpaste base comprising a polishing agent, humectant, and water.

When the product of the invention is a tooth powder, it comprises about 0.1% to about 30% zinc compound capable of furnishing zinc ions, and about 0.1% to about 30% of an enzyme preparation selected from the group consisting of proteases, carbohydrases, lipases, and mixtures thereof, said zinc compound and said enzyme preparation being incorporated in a compatible powder base comprising a dental polishing agent.

When the product of the invention is a ready-to-use mouthwash, it comprises about 0.01% to about 5% of a zinc compound and about 0.0001% to about 5% of an enzyme preparation which may be a protease, a carbohydrase, a lipase or mixtures thereof. Enzyme preparations suitable for use at low levels, i.e., at about 0.0001% to about 0.2% are rather high in enzymatic activity. The zinc compound and enzyme preparation are dissolved or suspended in a compatible aqueous vehicle comprising water, and optionally (1) a surfactant, (2) a suspending agent, and (3) a non-aqueous liquid substance, such as glycerine, ethyl alcohol, propylene glycol, 1,3-butylene glycol, and mixtures thereof, having the functions of bodying agents or flavor modifiers. When present in the composition the non-aqueous liquid substance will usually be in the proportion of about 1% to about 50%, these percentages being based on the weight of the compatible aqueous vehicle.

It is within the purview of this invention to provide a dry-appearing particulate mixture of a zinc compound and an enzyme preparation of the classes described hereinbefore. The mixture finds utility as a concentrate for incorporation in a toothpaste or tooth powder composition, or for dilution with water or with water in conjunction with a non-aqueous liquid substance such as ethyl alcohol glycerol, propylene glycol, 1,3-butylene glycol, etc. to form a mouthwash.

The invention also contemplates a substantially water-free fluid suspension comprising an orally acceptable, substantially non-aqueous, liquid medium having incorporated therein from about 0.01% to about 15% zinc ions furnished by a non-enzyme bound, pharmaceutically acceptable zinc compound, and from about 0.01% to about 30% of a cosmetically acceptable enzyme preparation selected from the group consisting of proteases, carbohydrases, lipases, and mixtures thereof.

The zinc compound and enzyme in the aforementioned mixture will be present within a range of ratios consonant with the percentages set forth hereinbefore for ready-to-use oral preparations. For example a particulate mixture of 100 parts by weight of a zinc compound and 1 part by weight of a high-active enzyme preparation can be diluted with 9899 parts of water to provide a mouthwash containing 0.01% of a zinc compound and 0.0001% of an enzyme preparation. Other suitable ratios are set forth in the following Table I.

TABLE I

| Parts Zn Compound (A) | Parts Enzyme Preparation (B) | Ratio (A) to (B) in mixture | Parts H$_2$O with which mixture may be diluted (based on A + B) | Final Composition | |
|---|---|---|---|---|---|
| | | | | % Zn Cmpd. | % Enzyme Preparation |
| 5.0 | 0.0001 | 50,000 | 94.9999 | 5.0 | 0.0001 |
| 0.01 | 5.0 | 1/500 | 94.99 | 0.01 | 5.0 |
| 1 | 1 | 1 | 18 | 5.0 | 5.0 |
| 1 | 300 | 1/300 | 699 | 0.1 | 30.0 |
| 30,000 | 1 | 30,000 | 69,999 | 30 | 0.001 |
| 1 | 40 | 1/40 | 159 | 0.5 | 20 |
| 20 | 20 | 1 | 60 | 20 | 20 |
| 40 | 1 | 40 | 159 | 20 | 0.5 |

In the foregoing tabulation it is seen that ratios of zinc compound to enzyme preparation suitable for preparing a mixture intended to be diluted with a liquid or solid diluent to form a ready-to-use oral preparation range from 50,000:1 to 1:500, usually about 20,000:1 to about 1:200.

The particulate mixture of zinc compound and enzyme preparation may be admixed with a solid compatible diluent in any desired proportion prior to dilution to form a mouthwash, or prior to incorporation in a toothpaste or tooth powder. Suitable solid diluents are starch, NaCl, sodium acetyl salicylate, a dentifrice polishing agent, etc.

The ratio of zinc compound to enzyme preparation in the particulate mixtures will be such that the amount of enzyme is sufficient to coact with the zinc compound to provide, when the particulate mixture is diluted to form a ready-to-use oral preparation, an improved antiplaque and anticalculus composition.

The percentage of zinc compound in the ready-to-use oral products of this invention is such as to provide from about 0.01% to about 10% zinc ion. Higher levels, e.g., up to about 20% zinc ion and even higher in particulate compositions, may be present in the more concentrated compositions prepared for dilution before use. The zinc ion content of the zinc compounds useful in the products of this invention usually range from about 10% to about 50% but may range from about 10% to about 80%, the latter being the zinc content of zinc oxide.

The zinc compounds and the enzyme preparations have wide ranges of zinc content and active enzyme content respectively. Thus in order to provide the desired percentages of zinc ion and active enzyme, it is necessary to employ the several useful zinc compounds and enzyme preparations over wide percentage ranges. Those skilled in the art can readily ascertain the zinc ion content of the zinc compound and the active enzyme content of the enzyme preparation and calculate the desired proportions to use in the oral products of the instant invention.

No more enzyme than needed will normally be used. In ready-to-use mouthwashes in particular the enzyme content will be relatively low.

Substantially water-free fluid suspensions are encompassed by the instant invention. These are intended to provide a more stable fluid medium for the enzymes and moreover are intneded to be diluted before use. The substantially water-free fluid suspensions comprise an orally acceptable substantially non-aqueous medium having incorporated therein from about 0.01% to about 15% zinc ions furnished by a non-enzyme-bound pharmaceutically acceptable zinc compound and from about 0.01% to about 30% of a cosmetically acceptable enzyme preparation selected from the group consisting of proteases, carbohydrases, lipases, and mixtures thereof. The enzyme content of this type of product can be higher than in a ready-to-use product.

Toothpastes and tooth powder formulations also commonly contain a soap or synthetic detergent. It is usual in commercial dentifrice formulations, as well as in mouthwash formulations, to provide sufficient foaming action to satisfy a marked consumer preference for this property. A preferred foaming agent is sodium lauryl sulfate. However, many other detergents can be used, such as those listed in *Accepted Dental Therapeutics* 1969–1970. These include sodium alkyl sulfoacetate, sulfocolaurate, sodium lauroyl sarcosinate, and dioctyl sodium sulfosuccinate. Denaturation of the enzyme by the surface active agent is, of course, to be avoided. This may be done by means known to the art, for example by selecting enzyme-detergent combinations wherein the detergent is known to have a minimal effect on the particular enzyme to be used.

Plaque and calculus deposition on artificial dentures closely resemble that which forms on the natural dentition. The combination of zinc salt and hydrolytic enzyme of this invention is suited to use for the cleansing of artificial dentures. It may be employed as a powdered composition to be dissolved or dispersed in water for use in a conventional way, as a paste or suspension to be brushed onto the denture appliance, with or without an abrasive, or in any other convenient and suitable way known to the art.

The present invention may be further understood by the following Examples, which are illustrative, but not limitative, of the invention.

EXAMPLE 1

To evaluate the effect of proteolytic and other enzymes on the deposition of plaque and calculus, studies were conducted wherein the effect of these enzymes on plaque and calculus formation were evaluated with the aid of an artificial calculus-forming system. The experimental technique is described in an article by S. Wah Leung entitled, "A New Method for the In Vitro Production of Artificial Calculus," J. Periodontology, Vol. 28, page 317 (1956).

In principle, this method involves the dipping of extracted teeth or glass plummets in and out of saliva, or other calculogenic material such as porcine submaxillary gland extract, allowing time for the saliva to dry partially on the surface of the tooth or plummet. After a three to five day dipping period, a dental plaque-like deposit is evident, and after fourteen to twenty-eight days of dipping, a calculus-like crystalline hydroxyapatite deposit is found on the surface of the plummet. By treating the plummets daily with potential anticalculus agents, one can compare the type and extent of deposit appearing on the plummets. In this manner, observations of plaque or calculus formation can be made. The formation of calculus is normally characterized by examining the deposits formed by X-ray crystallography. This examination will show whether the deposits found on the plummet are amorphous or have developed the X-ray pattern characteristic of crystalline hydroxyapatite.

In the screening tests employed in these examples, the calculogenic substance is procine submaxillary gland extract containing added calcium and phosphate salts. After repeated dipping for a period of 8 days, treating the plummets once per day (generally for 1 minute) the plummets are examined for accumulation of deposit. The amount of accumulated deposit is rated both visually and by weight. The amount of deposit visually observed is graded as follows:

0 = no visible deposit
1 = very slight deposit
2 = light deposit
3 = medium deposit (control plummet)
4 = heavy deposit In addition, the deposits found on the plummets are examined by X-ray analysis to determine whether they exhibit the characteristic bands associated with the presence of hydroxyapatite crystalline material. The results obtained are presented in Table II.

It is evident from these results that a combination of a zinc compound and an enzyme provides excellent antiplaque and anticalculus effectiveness under conditions representing the relatively short contact time encountered in normal day-to-day use of oral hygiene products, e.g., toothpastes and mouthwashes, and that prior-art compositions i.e., a zinc compound or an enzyme alone, are inferior to the aforementioned combination in antiplaque and anticalculus effectiveness.

TABLE II

| Agent | Concentration | Carrier | Aver. Visual Rating | % Dry Wt. Reduction | X-ray Examination |
|---|---|---|---|---|---|
| Papain | 1.0% | Water | 3.0 | 2.5 | HA* (medium) |
| Papain + | 1.0% | | | | |
| Zinc phenosulfonate | 1.0% | Water | 2.5 | 31.4 | HA (very weak) |
| Amylase | 0.3% | Water | 4.0 | −93.0** | HA (weak) |

TABLE II-continued

| Agent | Concentration | Carrier | Aver. Visual Rating | % Dry Wt. Reduction | X-ray Examination |
|---|---|---|---|---|---|
| Amylase + | 0.3% | | | | |
| Zinc phenolsulfonate | 1.0% | Water | 2.0 | 37.8 | Amorphous |
| Alcalase | 0.3% | Water | 3.0 | −22.0 | HA (strong) |
| Alcalase + | 0.3% | | | | |
| Zinc phenolsulfonate | 1.0% | Water | 2.0 | 35.9 | Amorphous |
| Amylase + | 0.3% | | | | |
| Alcalase | 0.3% | Water | 2.5 | −26.0 | HA (strong) |
| Amylase + | 0.3% | | | | |
| Alcalase + | | | | | |
| Zinc phenolsulfonate | 1.0% | Water | 2.0 | 30.3 | Amorphous |
| Cellzyme A | 0.3% | Water | 2.5 | 30.5 | Amorphous |
| Cellzyme A + | 0.3% | | | | |
| Zinc phenolsulfonate | 1.0% | Water | 2.0 | 34.6 | Amorphous |
| Lipase 4000 | 0.3% | Water | 1.5 | −3.0 | Amorphous |
| Lipase 4000 + | 0.3% | | | | |
| Zinc phenolsulfonate | 1.0% | Water | 2.5 | 15.9 | Amorphous |
| Mylase 100 | 0.3% | Water | 3.0 | −2.6 | Amorphous |
| Mylase 100 + | 0.3% | | | | |
| Zinc phenolsulfonate | 1.0% | Water | 2.5 | 10.3 | Amorphous |
| Mylase W | 0.3% | Water | 2.5 | 0.4 | HA (strong) |
| Mylase W + | 0.3% | | | | |
| Zinc phenolsulfonate | 1.0% | Water | 3.0 | 0 | Amorphous |
| Lipase B | 0.3% | Water | 3.0 | −6.0 | Amorphous |
| Lipase B + | 0.3% | | | | |
| Zinc phenolsulfonate | 1.0% | Water | 2.0 | 6.6 | Amorphous |
| Lipase 448 | 0.3% | Water | 1.5 | 33.7 | Amorphous |
| Lipase 448 + | 0.3% | | | | |
| Zinc phenolsulfonate | 1.0% | Water | 2.0 | 43.9 | Amorphous |
| Rhozyme K-2 | 0.3% | Water | 3.0 | 6.6 | Amorphous |
| Rhozyme K-2 + | 0.3% | | | | |
| Zinc phenolsulfonate | 1.0% | Water | 2.5 | 25.3 | Amorphous |
| Rhozyme P-11 | 0.3% | Water | 2.5 | 13.3 | HA (strong) |
| Rhozyme P-11 + | 0.3% | | | | |
| Zinc phenolsulfonate | 1.0% | Water | 2.0 | 39.6 | Amorphous |
| M-Zyme | 0.3% | Water | 3.0 | −15.0 | HA (strong) |
| M-Zyme + | 0.3% | | | | |
| Zinc phenolsulfonate | 1.0% | Water | 3.0 | −2.0 | Amorphous |
| Zn phenolsulfonate | 1.0% | Water | 2.5 | 0 | Amorphous |

*HA = hydroxyapatite
**A negative value indicates an increase in weight

The enzyme preparations referred to in Example 1 are described hereinbefore.

EXAMPLE 2

A clinical test of compositions within the invention is performed as follows:

Test Protocol

After breakfast for the first seven days of the test each subject brushes for one minute with a control dentifrice and then rinses for 30 seconds with his assigned rinse. The subject rinses again (but does not brush) after lunch. After this first phase there follows a 3 day period during which each subject refrains from all brushing but continues the rinsing regimen. On the eleventh day the subject refrains from breakfast and plaque accumulation is scored.

The plaque is disclosed with a Basic Fuchsin solution. A scoring system of 0 (absence of plaque) to 3 (heavy plaque) is used for each facial, gingival and interproximal surface. All teeth present are scored. Scoring is confined to the buccal surfaces.

The compositions of the oral rinses are:

| Ingredient | Wt. % |
|---|---|
| Enzyme AP | 0.0042* |
| Flavor | 0.125 |
| Saccharin | 0.020 |
| Distilled H$_2$O | 99.8508 |
| 0.8% Suspension of heat-denatured Enzyme AP | 0.500** |
| Flavor | 0.125 |
| Saccharin | 0.020 |
| Distilled H$_2$O | 99.355 |
| Enzyme AP | 0.0042 |
| Zinc Phenolsulfonate | 1.000 |
| Flavor | 0.125 |
| Saccharin | 0.020 |
| Distilled H$_2$O | 98.8508 |
| Zinc Phenolsulfonate | 1.000 |
| Flavor | 0.125 |
| Saccharin | 0.020 |
| Distilled H$_2$O | 98.855 |

*The activity is 2.4 million units per gm. at pH 7. Therefore, 1/240 gm. in 100 ml of rinse per person per day gives the desired exposure of 10,000 units per day.
**A 0.8% Suspension of active enzyme is heated at 100° C. for 15 minutes. An aliquot is assayed to confirm total loss of proteolytic activity.

Examiner precision is checked by randomly selecting subjects to be rescored. Total mouth scores vary by less than 1%. Slight variation is noted on individual surfaces. The average number of buccal surfaces scored is 78.6.

TABLE III

MEAN PLAQUE SCORE REDUCTION

| Subject | Score Denatured Enzyme* | Score Enzyme* | % Reduction by Enzyme | Score ZnPS** | % Reduction by ZnPS | Score ZnPS + Enzyme | % Reduction by ZnPS + Enzyme |
|---|---|---|---|---|---|---|---|
| A | 2.38 | 2.42 | −2 | — | | 1.54 | 35 |
| B | 2.42 | 2.38 | 2 | 1.91 | 21 | 1.80 | 26 |
| C | 1.14 | 1.40 | −23 | 0.66 | 42 | 0.61 | 47 |
| D | 1.74 | 2.12 | −22 | 0.85 | 51 | 0.29 | 83 |
| E | 1.81 | 1.77 | 2 | 1.83 | −1 | 1.00 | 45 |
| Avg. φ | | | −10 | | 31 | | 50 |

*Enzyme = Proteolytic enzyme AP from Bacillus subtilis (Monsanto)
**ZnPS = Zinc Phenolsulfonate
φ Subjects B-E only It will be observed that the in vivo test procedure which provides the results set forth in Table III show that zinc phenolsulfate has activity in reducing plaque formation, and that the enzyme tested does not. The results for both agents are variable, due to the variability in natural biological systems, such as variability in diet, natural oral flora, and other factors. The in vivo tests reflect the total biological effect, and the results in Table III clearly show the advantage of mixtures of a zinc compound and an enzyme in the reduction of plaque formation.

Reference to Table II shows that the same zinc compound discussed above, namely zinc phenolsulfonate, is completely ineffective to inhibit the deposit of calculus-like material in in vitro tests, which reflect an important part of the biological reaction, but unlike in vivo tests, are not influenced by the natural variations in individual oral biological behavior.

EXAMPLE 3

A substantially water-free mouthwash concentrate may be formulated having the composition shown below. The composition may be diluted with water as desired just prior to use.

| | % |
|---|---|
| Zinc sulfate | 3.00 |
| Enzyme (protease derived from Bacillus subtilis) | 0.05 |
| Flavoring substance | 0.50 |
| Saccharin | 0.40 |
| Glycerol | 96.05 |
| | 100.00 |

Sorbitol or ethyl alcohol may be substituted for glycerol. When diluted for example, 1:10 with water, an effective mouthwash is obtained. Zinc sulfate in the proportion of 3.00% corresponds to 1.2% zinc ion.

EXAMPLE 4

A toothpaste is prepared having the following composition.

| | % |
|---|---|
| Silica xerogel* | 14.000 |
| Silica aerogel* | 8.000 |
| Sodium carboxymethylcellulose | 0.300 |
| Saccharin | 0.200 |
| Sodium benzoate | 0.081 |
| Polyethylene glycol (m.w.=400) | 5.000 |
| Colorants | 0.536 |
| Flavoring substance | 1.250 |
| Hexachlorophene | 0.050 |
| Chloroform | 0.800 |
| Sodium lauryl sulfate | 1.470 |
| Enzyme AP | 0.250 |
| Zinc phenolsulfonate | 1.000 |
| Sorbitol solution (70% in water) | 48.148 |
| Glycerine | 18.915 |
| | 100.000 |

The product contains about 15% water.
*Suitable silica xerogels and aerogels are obtainable from the Davison Chemical Division of the W. R. Grace Company under the trademarks "Syloid 63" and "Syloid 244" respectively.

The foregoing composition may be expressed in more generic terms as follows:

| | % |
|---|---|
| Silica xerogel | 14.00 |
| Silica aerogel | 8.00 |
| Binder | 0.30 |
| Humectants and water | 72.06 |
| Protease enzyme preparation | 0.25 |
| Zinc phenolsulfonate | 1.00 |
| Sodium lauryl sulfate | 1.47 |
| Chloroform | 0.80 |
| Colorant, flavoring substance, sweetener, halogenated germicide, preservative | 2.12 |
| | 100.00 |

When the toothpaste is stored for 29 days at room temperature, the enzyme activity decreases somewhat from the initial level of 0.250%, i.e., it becomes 0.202% (2.02 mg. per gm. of toothpaste) and when stored for 29 days at 37° C. the enzyme activity is 0.187% (1.87 mg. per gm. of toothpaste), indicating satisfactory stability.

EXAMPLE 5

Following is the composition of a toothpaste falling within the invention.

| | % |
|---|---|
| Silica xerogel* | 14.00 |
| Sodium carboxymethylcellulose | 0.30 |
| Saccharin | 0.20 |
| Sodium benzoate | 0.08 |
| Polyethylene glycol (m.w.=400) | 5.00 |
| Colorants | 0.53 |
| Flavoring substance | 1.25 |
| Sorbitol solution (70% in water) | 47.20 |
| Dextranase (435 units/gm.) | 0.25 |
| Zinc citrate | 2.00 |
| Sodium lauryl sulfate | 1.47 |
| Glycerine | 19.72 |
| | 100.00 |

*The silica xerogel and aerogel are as defined in Example 4.

The dextranase activity of the toothpaste of Example 5 does not decrease after 2½ months' storage at room temperature.

EXAMPLE 6

A toothpaste may be prepared in accordance with the invention, having a silica xerogel as the sole polishing agent, as shown below.

|  | % |
|---|---|
| % Silica xerogel* | 25.00 |
| % Sodium carboxymethylcellulose | 0.60 |
| % Sorbitol solution (70% in water) | 60.12 |
| % Sodium benzoate | 0.08 |
| % Saccharin | 0.20 |
| % Colorants | 0.53 |
| % Flavor | 1.90 |
| % Sodium hydroxide solution (30%) | 0.07 |
| % Sodium lauryl sulfate solution in glycerol (21%) |  |
| % Lipolytic enzyme** | 0.50 |
| % Zinc citrate | 4.00 |
|  | 100.00 |

*As defined in Example 4.
**Lipase 448, defined hereinbefore.

EXAMPLE 7

Following is an example of a substantially water-free toothpaste having a composition within the invention.

|  | % |
|---|---|
| % Silica xerogel* | 14.70 |
| % Silica aerogel* | 10.39 |
| % TiO$_2$ | 0.30 |
| % Saccharin | 0.20 |
| % Polyetheylene glycol (m.w.=400) | 39.93 |
| % Flavoring substance | 0.92 |
| % Enzyme AP** | 0.25 |
| % Zinc Phenolsulfonate | 0.10 |
| % Sodium lauryl sulfate | 2.33 |
| % Glycerine | 30.88 |
|  | 100.00 |

*As defined in Example 4.
**As defined in Example 2.

This product retains 100% of its proteolytic enzyme activity after storing 22 days at 37° C., although the toothpaste is not as pleasant to use as the other toothpaste compositions of the invention because of the absence of water.

All percentages given herein and in the appended claims are by weight on the whole composition basis unless otherwise specified.

EXAMPLE 8

The following combination of zinc compounds and enzyme are tested for antiplaque and anticalculus effectiveness by the procedure described in Example 1. The results in Table IV show that a variety of zinc compounds are effective at concentrations in an aqueous medium within the overall range of 0.2% to 5%.

TABLE IV

| Agent | Concentration | Carrier | Average % Dry Wt. Reduction | X-ray Examination |
|---|---|---|---|---|
| Trypsin(a) | 0.1% | Water | 7.5 | Amorphous |
| Zn citrate | 5.0% | Water | 9.0 | Amorphous |
| ZnO | 0.2% | Water | −1.4(b) | Amorphous |
| Trypsin + Zn citrate | 0.1% 5.0% | Water | 21.1 | Amorphous |
| Trypsin + ZnO | 0.1% 0.2% | Water | 17.6 | Amorphous |
| Trypsin | 0.3% | Water | 9.3 | Amorphous |
| Trypsin + ZnO | 0.3% 0.2% | Water | 19.3 | Amorphous |
| ZnCl$_2$ | 0.25% | Water | −18.5 | Amorphous |
| Trypsin + ZnCl$_2$ | 0.3 0.25 | Water | 50.3 | Amorphous |
| Water only | — | — | 0 | hydroxyapatite (weak to medium) |

(a)Lyophilized Trypsin TRL9FA (Worthington), 200 μ/mg, used in conjunction with 0.01M Cl added as NaCl.
(b)A negative value indicates an increase in deposit weight as compared with the control.

Having described the invention, many modifications thereof will be apparent to those skilled in the art, and the invention is to be limited only by the scope of the appended claims.

What is claimed is:

1. A fluoride-free mouthwash capable or reducing dental plaque and calculus consisting essentially of:
   (a) about 0.01% to about 5% of a non-enzyme bound, pharmaceutically acceptable zinc compound selected from the group consisting of zinc acetate, benzoate, borate, carbonate, citrate, dl-lactate trihydrate, phenolsulfonate, silicate, an alkanoate having 8 to 18 carbon atoms, salicylate, stannate, sulfate, tannate and titanate;
   (b) about 0.0001% to about 5% of an enzyme preparation selected from the group consisting of a protease, a carbohydrase, a lipase and mixtures thereof;
   (c) 0 to about 50% of a non-aqueous liquid selected from the group consisting of ethyl alcohol, propylene glycol, 1,3-butylene glycol and mixtures thereof;
   (d) 0 to 2% of surfactants and suspending agents; and
   (e) the balance water.

2. The mouthwash of claim 1 wherein said zinc salt is zinc phenolsulfonate.

3. The mouthwash of claim 1 wherein said zinc salt is zinc citrate.

4. The mouthwash of claim 1 wherein said non-aqueous liquid is ethyl alcohol.

5. The mouthwash of claim 1 wherein said enzyme preparation is a protease derived from *Bacillus subtilis*.

6. The mouthwash of claim 1 wherein said enzyme preparation is a lipase derived from animal pancreas.

7. The mouthwash of claim 1 wherein said enzyme preparation is an amylase.

8. A substantially water-free and fluoride-free fluid suspension for use as a mouthwash concentrate comprising:
   (a) about 0.01% to about 15% zinc ions furnished by a non-enzyme bound, pharmaceutically acceptable zinc compound selected from the group consisting of zinc acetate, benzoate, borate, carbonate, citrate, dl-lactate trihydrate, phenolsulfonate, silicate, an alkanoate having 8 to 18 carbon atoms, salicylate, stannate, sulfate, tannate and titanate;
   (b) about 0.01% to about 30% of a cosmetically acceptable enzyme preparation selected from the group consisting of protease, a carbohydrase, a lipase and mixtures thereof; and
   (c) a non-aqueous liquid base selected from the group consisting of glycerol and ethyl alcohol.

9. The fluid suspension of claim 8 wherein said liquid base is glycerol.

10. The fluid suspension as in claim 8 wherein said zinc compound is zinc phenol sulfonate.

11. The fluid suspension of claim 8 wherein said enzyme preparation is a protease derived from *Bacillus subtilis*.

* * * * *

UNITED STATES PATENT AND TRADEMARK OFFICE
CERTIFICATE OF CORRECTION

PATENT NO. : 4,152,418  Page 1 of 2
DATED : May 1, 1979
INVENTOR(S) : Morton Pader It is certified that error appears in the above-identified patent and that said Letters Patent are hereby corrected as shown below:

Other Publications, Ref. 3, line 6: "Canero" should read -- Cancro --.

Column 4, line 34: "hibiting" should read -- inhibiting --.

Column 8, line 49: "coating" should read -- coacting --.

Column 10, line 12: The heading "Among the useful carbohydrases are:" has been printed twice. The second should be deleted.

Column 10, line 30: "Among the lipases useful in the invention are:" should have been printed in the same way as line 10, i.e. in larger print with solid lines above and below the sentence.

Column 11, line 3: "as desired" is a continuation of the sentence in the table on the preceding page and should not be separated by a solid line above it.

UNITED STATES PATENT AND TRADEMARK OFFICE
CERTIFICATE OF CORRECTION

PATENT NO. : 4,152,418           Page 2 of 2

DATED : May 1, 1979

INVENTOR(S) : Morton Pader

It is certified that error appears in the above—identified patent and that said Letters Patent are hereby corrected as shown below:

Column 14, line 32:     "procine" should read -- porcine --.

Column 16:     In the table, each of the four formulations should be separated by space or a solid line after "Distilled Water".

Signed and Sealed this

Eighteenth Day of December 1979

[SEAL]

Attest:

SIDNEY A. DIAMOND

Attesting Officer      Commissioner of Patents and Trademarks